(12) United States Patent
Roizin et al.

(10) Patent No.: US 10,788,375 B2
(45) Date of Patent: Sep. 29, 2020

(54) APPARATUS, SYSTEM AND METHOD OF A TEMPERATURE SENSOR

(71) Applicant: TOWER SEMICONDUCTOR LTD., Migdal Haemek (IL)

(72) Inventors: Yakov Roizin, Afula (IL); Menachem Vofsy, Kiriat Tivon (IL); Alexey Heiman, Ramat Yishai (IL); Yossi Rosenwaks, Hod Hasharon (IL); Klimentiy Shimanovich, Ramat Gan (IL); Yhonatan Vaknin, Yoqneam Illit (IL)

(73) Assignee: TOWER SEMICONDUCTOR LTD., Migdal Haemek (IL)

( * ) Notice: Subject to any disclaimer, the term of this patent is extended or adjusted under 35 U.S.C. 154(b) by 370 days.

(21) Appl. No.: 15/834,505

(22) Filed: Dec. 7, 2017

(65) Prior Publication Data

US 2019/0178725 A1 Jun. 13, 2019

(51) Int. Cl.
| | |
|---|---|
| *G01K 7/01* | (2006.01) |
| *H01L 29/16* | (2006.01) |
| *G01N 33/00* | (2006.01) |
| *H01L 23/34* | (2006.01) |
| *G01K 7/00* | (2006.01) |
| *G01K 7/16* | (2006.01) |
| *H01L 29/06* | (2006.01) |
| *H01L 29/40* | (2006.01) |
| *H01L 29/775* | (2006.01) |

(52) U.S. Cl.
CPC ............... *G01K 7/01* (2013.01); *G01K 7/00* (2013.01); *G01K 7/16* (2013.01); *G01N 33/0016* (2013.01); *H01L 23/345* (2013.01); *H01L 29/16* (2013.01); *G01K 2211/00* (2013.01); *H01L 29/0673* (2013.01); *H01L 29/408* (2013.01); *H01L 29/775* (2013.01)

(58) Field of Classification Search
None
See application file for complete search history.

(56) References Cited

U.S. PATENT DOCUMENTS

| | | | |
|---|---|---|---|
| 7,439,575 | B2 | 10/2008 | Roizin et al. |
| 7,489,024 | B2 | 2/2009 | Socher et al. |
| 8,007,727 | B2 | 8/2011 | Shalev et al. |
| 8,080,456 | B2 | 12/2011 | Barwicz et al. |
| 9,134,191 | B2 | 9/2015 | Rahajandraibe et al. |

(Continued)

OTHER PUBLICATIONS

Akarvardar et al., "Depletion-All-Around Operation of the SOI Four-Gate Transistor", IEEE Transactions on Electron Devices, vol. 54, No. 2, Feb. 2007, pp. 323-331.

(Continued)

*Primary Examiner* — Matthew D Krcha
(74) *Attorney, Agent, or Firm* — Shichrur & Co.

(57) ABSTRACT

Some demonstrative embodiments include an apparatus of a temperature sensor to sense temperature, the apparatus including a first pad on a silicon substrate; a second pad on the silicon substrate; a silicon nanowire having a first end coupled to the first pad and a second end coupled to the second pad, the silicon nanowire configured to drive a current between the first pad and the second pad, the current depending at least on the temperature; and a charged dielectric layer covering at least three sides of the silicon nanowire.

21 Claims, 9 Drawing Sheets

(56) References Cited

U.S. PATENT DOCUMENTS

| | | | |
|---|---|---|---|
| 2008/0035983 A1* | 2/2008 | Sandhu | B82Y 10/00 257/316 |
| 2010/0065923 A1* | 3/2010 | Charles | H01L 29/2003 257/402 |
| 2011/0147802 A1* | 6/2011 | Colli | B82Y 10/00 257/253 |
| 2011/0198498 A1* | 8/2011 | Park | B82Y 15/00 250/330 |
| 2014/0034907 A1* | 2/2014 | Lee | G01N 27/06 257/24 |
| 2016/0003770 A1* | 1/2016 | Klootwijk | G01N 27/4146 73/31.06 |
| 2017/0241932 A1* | 8/2017 | Lee | G01N 27/127 |
| 2017/0356867 A1* | 12/2017 | Daunais | H01L 21/32055 |

OTHER PUBLICATIONS

Hashim et al, "Temperature Effect on I-V Characteristics of Si Nanowire Transistor", IEEE Colloquium on Humanities, Science and Engineering Research (CHUSER 2011) Penang, Dec. 5-6, 2011, 4 pages.

\* cited by examiner

APPARATUS, SYSTEM AND METHOD OF A TEMPERATURE SENSOR

TECHNICAL FIELD

Embodiments described herein generally relate to a temperature sensor.

BACKGROUND

A temperature sensor may be implemented in one or more devices to sense temperature.

BRIEF DESCRIPTION OF THE DRAWINGS

For simplicity and clarity of illustration, elements shown in the figures have not necessarily been drawn to scale. For example, the dimensions of some of the elements may be exaggerated relative to other elements for clarity of presentation. Furthermore, reference numerals may be repeated among the figures to indicate corresponding or analogous elements. The figures are listed below.

DETAILED DESCRIPTION

In the following detailed description, numerous specific details are set forth in order to provide a thorough understanding of some embodiments. However, it will be understood by persons of ordinary skill in the art that some embodiments may be practiced without these specific details. In other instances, well-known methods, procedures, components, units and/or circuits have not been described in detail so as not to obscure the discussion.

The terms "plurality" and "a plurality", as used herein, include, for example, "multiple" or "two or more". For example, "a plurality of items" includes two or more items.

References to "one embodiment", "an embodiment", "demonstrative embodiment", "various embodiments" etc., indicate that the embodiment(s) so described may include a particular feature, structure, or characteristic, but not every embodiment necessarily includes the particular feature, structure, or characteristic. Further, repeated use of the phrase "in one embodiment" does not necessarily refer to the same embodiment, although it may.

As used herein, unless otherwise specified the use of the ordinal adjectives "first", "second", "third" etc., to describe a common object, merely indicate that different instances of like objects are being referred to, and are not intended to imply that the objects so described must be in a given sequence, either temporally, spatially, in ranking, or in any other manner.

Some embodiments may be used in conjunction with various devices and systems, for example, an electronic device, a computing device, an integrated computing device, an integrated chip, electronic circuitry, a processing device, an electrical device, a sensor, a temperature sensor, a gas sensor, an Internet of Things (IoT) device, a processor, a memory device, an imaging device, a digital camera device, a video device, a camera module, a medical imaging device, a mobile computer, a laptop computer, a notebook computer, a tablet computer, a handheld computer, a handheld device, a Personal Digital Assistant (PDA) device, a handheld PDA device, a mobile or portable device, a consumer device, a Smartphone and the like.

The terms "substrate" and/or "wafer", as used herein, may relate to a thin slice of semiconductor material, for example, a silicon crystal, which may be used in fabrication of integrated circuits and/or any other microelectronic devices. For example, the wafer may serve as the substrate for the microelectronic devices, which may be built in and over the wafer.

The term "Integrated Circuit" (IC), as used herein, may relate to a set of one or more electronic circuits on a semiconductor material. For example, the electronic circuit may include electronic components and their interconnectors.

Figure 1:
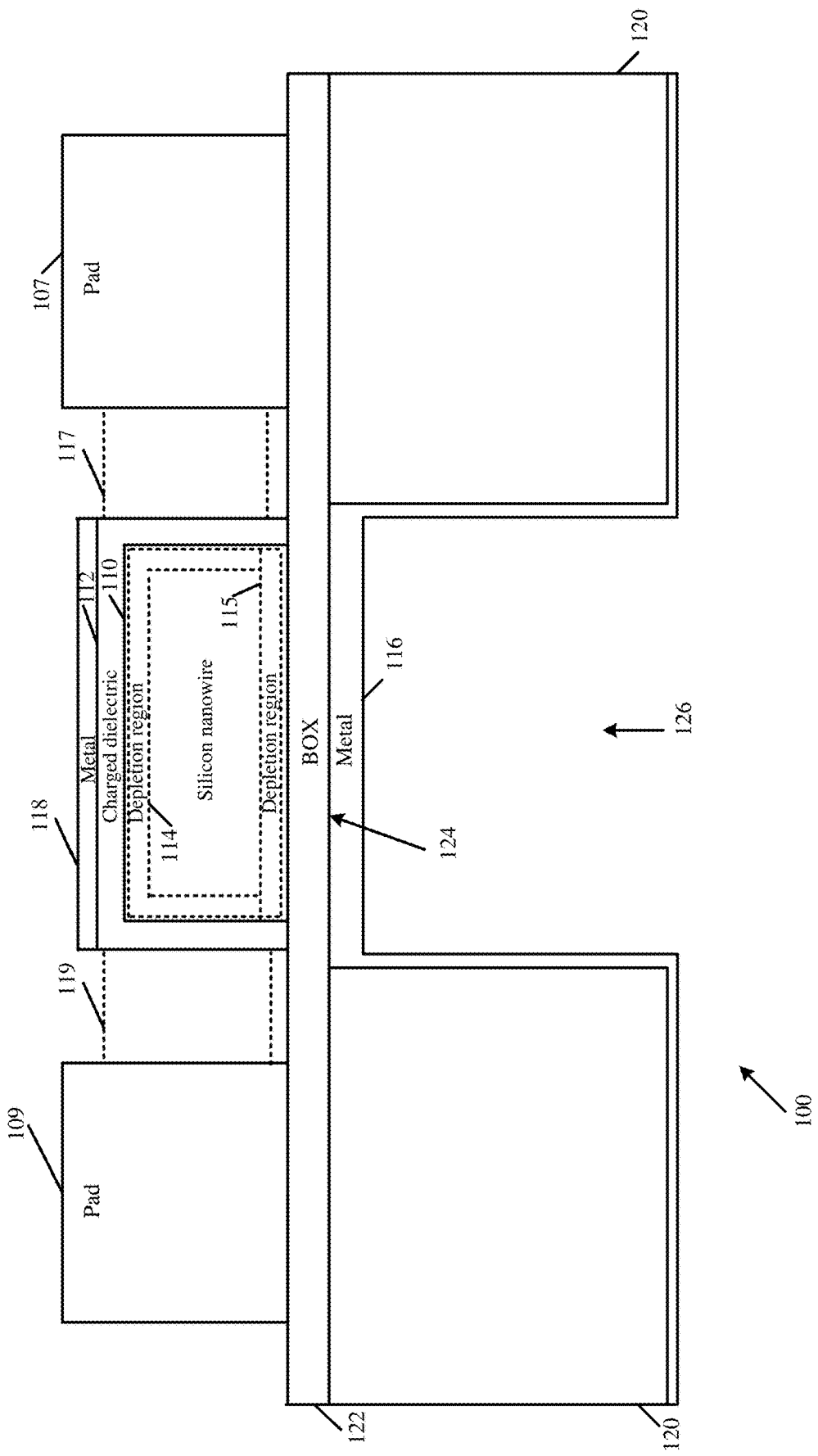
FIG. 1 is a schematic block diagram illustration of an apparatus, in accordance with some demonstrative embodiments.

Reference is made to FIG. 1, which schematically illustrates a block diagram of an apparatus 100, in accordance with some demonstrative embodiments.

In some demonstrative embodiments, apparatus 100 may include, or may be operable as, a temperature sensor configured to sense temperature, e.g., as described below.

In some demonstrative embodiments, apparatus 100 may include, or may be operable as, a gas sensor configured to sense a predefined type of gas, e.g., as described below.

In some demonstrative embodiments, apparatus 100 may include, or may be operable as, a heater, e.g., as described below.

In some demonstrative embodiments, apparatus 100 may include, or may be operable as, any other sensor, device and/or unit.

In some demonstrative embodiments, apparatus 100 may be implemented as part of an electronic device, e.g., as described below.

In some demonstrative embodiments, the electronic device may include an Internet of Things (IoT) device.

In some demonstrative embodiments, the electronic device may include a temperature sensing device, e.g., as described below.

In one example, the electronic device may include an IoT temperature-sensing device, e.g., as described below.

In some demonstrative embodiments, the electronic device may include a gas sensor, e.g., as described below.

In some demonstrative embodiments, the electronic device may include any other electronic device.

In some demonstrative embodiments, apparatus 100 may include an Integrated Circuit (IC).

In one example, the electronic circuit or the IC may include, may be part of, and/or may be implemented as part of the electronic device.

In some demonstrative embodiments, apparatus 100 may include, or may be operable as, the temperature sensor to sense temperature.

In some demonstrative embodiments, apparatus 100 may include a silicon nanowire 110 configured to sense the temperature, e.g., as described below.

In some demonstrative embodiments, silicon nanowire 110 may be formed on a silicon substrate 120, e.g., as described below.

In some demonstrative embodiments, silicon substrate 120 may include a Silicon On Insulator (SOI) substrate, e.g., as described below.

In some demonstrative embodiments, apparatus 100 may include a first pad 107 on silicon substrate 120, e.g., as described below.

In some demonstrative embodiments, apparatus 100 may include a second pad 109 on silicon substrate 120, e.g., as described below.

In some demonstrative embodiments, silicon nanowire 110 may have a first end 117 coupled to the first pad 107, e.g., as described below.

In some demonstrative embodiments, silicon nanowire 110 may have a second end 119 coupled to the second pad 109, e.g., as described below.

In some demonstrative embodiments, silicon nanowire 110 may be configured to drive a current between the first pad 107 and the second pad 109.

In some demonstrative embodiments, the current may be based at least on, may depend at least on, may be correlated at least to, may be related at least to, and/or may be controlled by the temperature, e.g., as described below.

In some demonstrative embodiments, silicon nanowire 110 may include an N-type silicon nanowire, e.g., as described below.

In other embodiments, silicon nanowire 110 may include a P-type silicon nanowire, e.g., as described below.

In some demonstrative embodiments, silicon nanowire 110 may be on the silicon substrate 120, e.g., as described below.

In other embodiments, silicon nanowire 110 may not be on the silicon substrate 120, e.g., as described below.

In some demonstrative embodiments, silicon substrate 120 may include a Buried Oxide (BOX) layer 122, and silicon nanowire 110 may be on the BOX layer 122, e.g., as described below.

In one example, silicon nanowire 110 may be formed from a silicon layer of the SOI (also referred to as the "device layer").

In some demonstrative embodiments, apparatus 100 may include a charged dielectric layer 112 at least partially covering silicon nanowire 110, e.g., as described below.

In some demonstrative embodiments, charged dielectric layer 112 may cover at least three sides of the silicon nanowire 110, e.g., as described below.

In some demonstrative embodiments, the charged dielectric layer 112 may be configured to create a depletion region 114 in a conductive channel of the silicon nanowire 110, e.g., as described below.

In some demonstrative embodiments, the charged dielectric layer 112 may include an Oxide Nitride Oxide (ONO) layer, or an Oxide Nitride (ON) layer, for example, when silicon nanowire 110 includes the N-type silicon nanowire, e.g., as described below.

In some demonstrative embodiments, the charged dielectric layer 112 may include an Ultra Violet (UV)-charged ONO layer, or a UV-charged ON layer, for example, when silicon nanowire 110 includes the N-type silicon nanowire, e.g., as described below.

In some demonstrative embodiments, the charged dielectric layer 112 may include a charged silicon dioxide layer, for example, when silicon nanowire 110 includes the P-type silicon nanowire, e.g., as described below.

In some demonstrative embodiments, the charged dielectric layer 112 may include an ionizing radiation charged silicon dioxide layer, for example, when silicon nanowire 110 includes the P-type silicon nanowire, e.g., as described below.

In other embodiments, the charged dielectric layer 112 may include any other additional or alternative layer, e.g., as described below.

In some demonstrative embodiments, apparatus 100 may include a backside gate 124 coupled to the silicon nanowire 110, e.g., as described below.

In some demonstrative embodiments, backside gate 124 may be in contact with the BOX layer 122, e.g., as described below.

In some demonstrative embodiments, backside gate 124 may be in an opening 126 in the silicon substrate, e.g., as described below.

In some demonstrative embodiments, backside gate 124 may be operable to control a size of a depletion region 115 in the conductive channel of the silicon nanowire 110, e.g., as described below.

In some demonstrative embodiments, apparatus 100 may be operable as a gas sensor to sense a predefined type of gas, e.g., as described below.

In some demonstrative embodiments, backside gate 124 may include a metal layer 116, e.g., as described below.

In some demonstrative embodiments, the metal layer 116 may be configured to react with the predefined type of gas.

In some demonstrative embodiments, the metal layer 116 may be configured to operate as a catalyst for gas sensing.

In one example, metal layer 116 may include at least Palladium and/or Platinum, and/or any other suitable material.

In one example, the silicon nanowire may be configured for use in various sensing systems, for example, in gas sensors. A high surface to volume ratio of the silicon nanowire may make the silicon nanowire, for example, suitable for sensing of low densities of molecules absorbed at the surfaces of the silicon nanowire. For example, a measured parameter may include a nanowire resistance of the silicon nanowire. One or more measurements may be performed, for example, using transistor configurations with additional electrodes, which may act as gates. The gates may help to define a charge carrier concentration, which may provide an increased sensing performance.

In one example, one or more parameters of silicon nanowire 110 may change, for example, when subject to presence of one or more types of gases, e.g., based on type of the gases and/or concentration of the gases. For example, silicon nanowire 110 may be used as temperature sensor, for example, to control temperature changes resulting from reaction with gases at the surfaces of silicon nanowire 110, e.g., to sense the presence of the gases. For example, exothermic reactions, e.g., gas oxidation reaction, at the surface of silicon nanowire 110 may be used, for example, to change the temperature. In such case, the surfaces of silicon nanowire 110 may be covered with Palladium, Platinum and/or any other suitable material, which may act as catalysts, e.g., for gas sensing.

In some demonstrative embodiments, the metal layer 116 may operate as a backside sensing area, e.g., to sense gas at the backside of silicon substrate 120.

In one example, a temperature of the metal layer 116 may change, for example, in reaction with the predefined type of gas, and, as a result, the current driven via nanowire 110 may change, thereby enabling to sense the predefined type of gas.

In some demonstrative embodiments, the silicon nanowire 110 may be covered with a metal layer 118, e.g., in addition to, or instead of, the metal layer 116.

In some demonstrative embodiments, the metal layer 118 covering silicon nanowire 110 may include at least Palladium and/or Platinum, or any other suitable material.

In one example, the Palladium and/or Platinum in metal layer 118 may operate as a catalyst for gas sensing. For example, the metal layer 118 covering silicon nanowire 110 may be configured to react with the predefined type of gas.

In one example, the metal layer 118 covering the silicon nanowire 110 may operate as a front side sensing area, e.g., to sense gas at the front side of silicon substrate 120.

In some demonstrative embodiments, apparatus 100 may include, or may be operable as, a heater, e.g., as described below.

In some demonstrative embodiments, the silicon nanowire 110 may be configured to be operable as a heater, for example, when a heating current is driven between the first pat 107 and the second pad 109 via the silicon nanowire 110.

In one example, one or more heaters, e.g., implementing nanowire 110, may be used, for example, to enhance a reaction in gas sensing devices.

In another example, one or more heaters, e.g., implementing nanowire 110, may be used, for example, as a separate thermometer for any other additional or alternative applications and/or devices.

Figure 2:
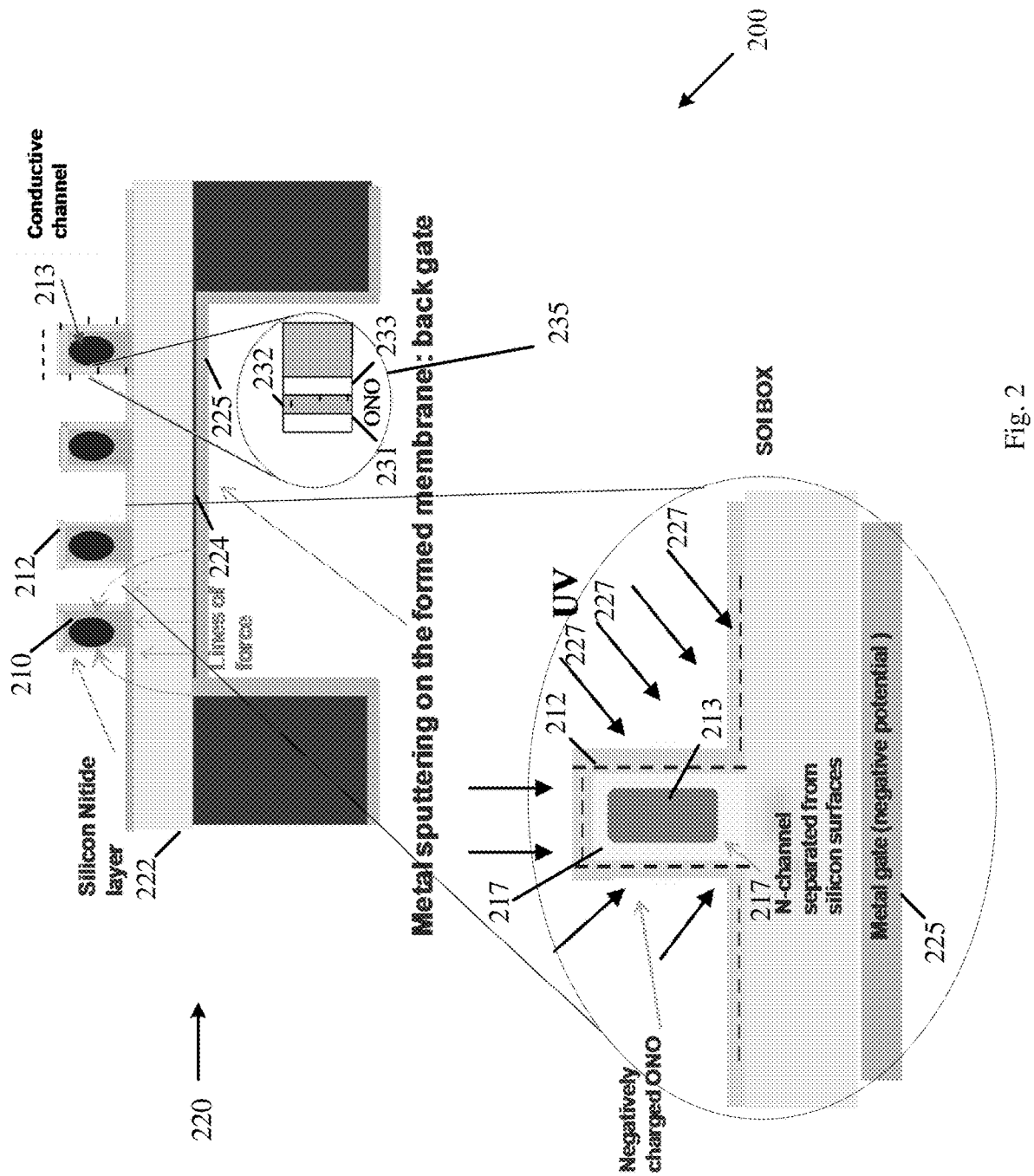
FIG. 2 is a schematic illustration of a cross section view of an apparatus, in accordance with some demonstrative embodiments.

Reference is made to FIG. 2, which schematically illustrates a cross section view of an apparatus 200, in accordance with some demonstrative embodiments.

In some demonstrative embodiments, as shown in FIG. 2, a silicon nanowire 210 may be formed on a SOI wafer 220.

In some demonstrative embodiments, silicon nanowire 210 may include an N-type silicon nanowire, e.g., as described below.

In other embodiments, silicon nanowire 210 may include a P-type silicon nanowire, e.g., as described below.

In some demonstrative embodiments, as shown in FIG. 2, a charged dielectric layer 212 may be deposited on one or more surfaces of silicon nanowire 210, e.g., as described below.

In some demonstrative embodiments, the charged dielectric layer 212 may include an ONO layer or an ON layer, e.g., when silicon nanowire 210 includes the N-type silicon nanowire.

In some demonstrative embodiments, as shown in FIG. 2, an ONO layer 235 may include a bottom oxide layer 231, a silicon nitride layer 232 and a top oxide layer 233.

In other embodiments, the ON layer may include the bottom oxide layer 231 and the silicon nitride layer 232, e.g., without the top oxide layer 233.

In other embodiments, a charged dielectric layer 212 may include a charged silicon dioxide layer, which may be deposited at one or more surfaces of silicon nanowire 210, e.g., when silicon nanowire 210 includes the P-type silicon nanowire.

In some demonstrative embodiments, as shown in FIG. 2, the backside of SOI wafer 220 may be etched to form a backside gate 224.

In some demonstrative embodiments, as shown in FIG. 2, the etching at the backside 224 of SOI wafer 220 may stop on a BOX layer 222 of SOI wafer 220.

In some demonstrative embodiments, BOX layer 222 may act as a dielectric of the backside gate 224.

In some demonstrative embodiments, as shown in FIG. 2, the backside of SOI wafer 220 may be covered with a metal layer 225, for example, to serve as the backside gate 224 for silicon nanowire 210.

In one example, metal layer 225 may be biased negatively with respect to silicon nanowire 210.

In some demonstrative embodiments, metal layer 225 may be configured to react with a predefined type of gas.

In one example, metal layer 225 may be formed of, or may at least partially include, Platinum, Palladium and/or any other conductive material, which may act as a catalyst, e.g., when reacting with the predefined type of gas.

In some demonstrative embodiments, as shown in FIG. 2, a top surface of SOI wafer 220 may be subject to UV light illumination 227, which may result in a negatively charged ONO layer 235.

In one example, ONO layer 235 may be charged by an external UV light, e.g., UV light illumination 227, for example, based on electron excitation from the valence band of silicon 220, and trapping of excited electrons in a silicon nitride layer 232 of the ONO layer 235.

In one example, the trapped charge, e.g., in the silicon nitride layer 232, may have an increased stability and/or may be able to withstand bake up procedures of above 150 Celsius (c), e.g., for years. For example, an effect of ONO charging may be used to control a conductive channel 213 in silicon nanowire 210, e.g., when silicon nanowire 210 is implemented by an N-type silicon nanowire.

In some demonstrative embodiments, nanowire 210 with an ONO layer 235 deposited at the surface of nanowire 210 may be illuminated by UV light illumination 227. A charge depletion region 217 may be created, e.g., at the Si—ONO surface, for example, if nanowire 210 includes an N-type silicon nanowire. As a result, conductive channel 213 may not be in contact with interfaces of silicon substrate 220.

In some demonstrative embodiments, charge depletion region 217 may be created, for example, if nanowire 210 includes a P-type silicon nanowire, and charged dielectric layer 212 includes positively charged dielectric films. For example, generation of positive charge in silicon dioxide films in silicon may be enabled, for example, by irradiating dielectric layer 212 with ionizing radiation.

In some demonstrative embodiments, silicon nanowire 210 may include, or may be implemented as, a physical silicon nanowire defined by lithography, and/or an electrostatically formed nanowire, e.g., as described below.

In some demonstrative embodiments, the physical nanowire, e.g., silicon nanowire 210, may be formed on SOI wafer 220 and may be covered by charged dielectric layer 212, which may be charged, for example, after the fabrication process, e.g., as described above.

In some demonstrative embodiments, the electrostatically formed nanowire may be formed by charging of dielectric layer 212, which may result in depletion region 217, e.g., at a part of a surface of silicon nanowire 210, that may separate the conductive channel 213 in silicon nanowire 210 from SOI wafer 220.

In one example, negatively charged Silicon Nitride of charged dielectric layer 212 may result in depletion region 217, for example, at the surface of silicon nanowire 210. As a result, electrons may be allowed to flow in the volume of silicon at a distance from Si—SiO2 interfaces, e.g., if silicon nanowire 210 includes the N-type silicon nanowire.

In another example, charged dielectric layer 212 including a positively charged silicon dioxide may result in depletion region 217, e.g., if silicon nanowire 210 includes the P-type silicon nanowire.

In some demonstrative embodiments, as shown in FIG. 2, silicon nanowire 210 may be capacitively coupled to a gate electrode, e.g., backside gate 224, which may be configured to control a size of depletion region 217.

In some demonstrative embodiments, as shown in FIG. 2, the silicon substrate may be removed from the back side of the SOI wafer 220, and the metal layer 225 may be sputtered at the BOX layer 222 from the back side of SOI wafer 220.

In some demonstrative embodiments, metal layer 225 may act as backside gate 224 to create depletion region 217, e.g., at a bottom surface of silicon nanowire 210.

In one example, the charging of charged dielectric layer 212, e.g., the ONO layer 235, and a bias of back gate 224 may be tuned, for example, to operate in a "sub-threshold" regime. According to this example, the current through the silicon nanowire 210 may have increased temperature sensitivity.

In some demonstrative embodiments, metal layer 225 may be configured to act as a catalyst for gas sensing.

Figure 3:
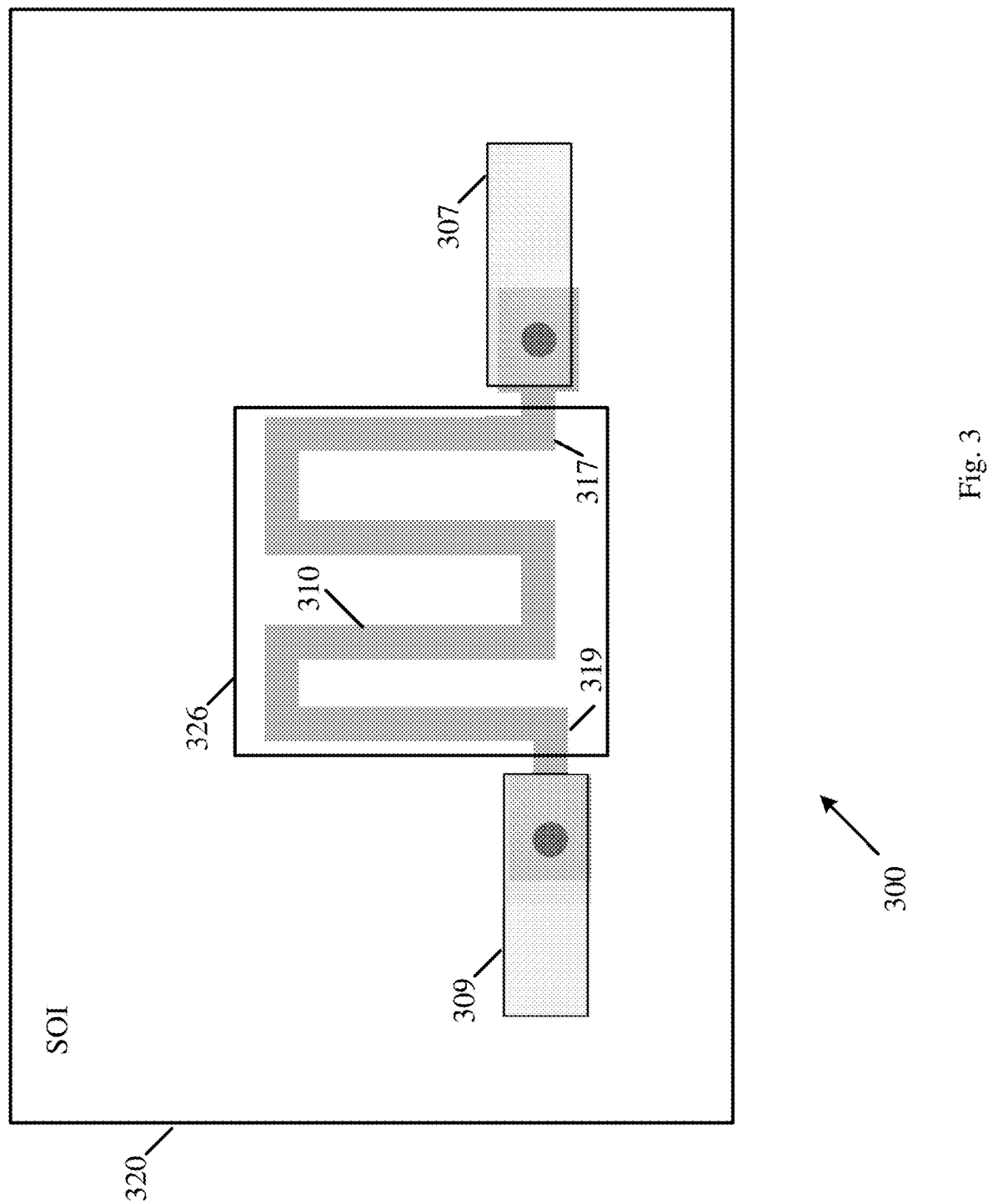
FIG. 3 is a schematic illustration of a top view of an apparatus, in accordance with some demonstrative embodiments.

Reference is made to FIG. 3, which schematically illustrates a top view of an apparatus 300, in accordance with some demonstrative embodiments.

In one example, apparatus 300 may include, or may be implemented as part of, a temperature sensor and/or a gas sensor.

In one example, FIG. 3 may include a top view of apparatus 200 (FIG. 2).

In some demonstrative embodiments, as shown in FIG. 3, apparatus 300 may include a silicon nanowire 310 on a SOI wafer 320.

In some demonstrative embodiments, as shown in FIG. 3, a first end 317 of silicon nanowire 310 may be coupled to a first pad 307, and a second end 319 of silicon nanowire 310 may be coupled to a second pad 309.

In some demonstrative embodiments, first pad 307 and second pad 309 may reside on SOI wafer 320.

In some demonstrative embodiments, SOI wafer 320 may include a BOX layer 326.

In some demonstrative embodiments, as shown in FIG. 3, silicon nanowire 310 may be on the BOX layer 326, for example, while first pad 307 and second pad 309 may be on bulk silicon of SOI wafer 320.

In one example, silicon nanowire 310 may be operable as a heater, for example, when a heating current is to be driven between the first pad 307 and second pads 309 via the silicon nanowire 310.

In one example, silicon nanowire 310 may be operable as a temperature sensor, for example, based on current to be driven between the first pad 307 and second pads 309 via the silicon nanowire 310.

In one example, silicon nanowire 310 may be operable as a gas sensor, for example, when a heating current to be driven between the first pad 307 and second pads 309 via the silicon nanowire 310.

Figure 4:
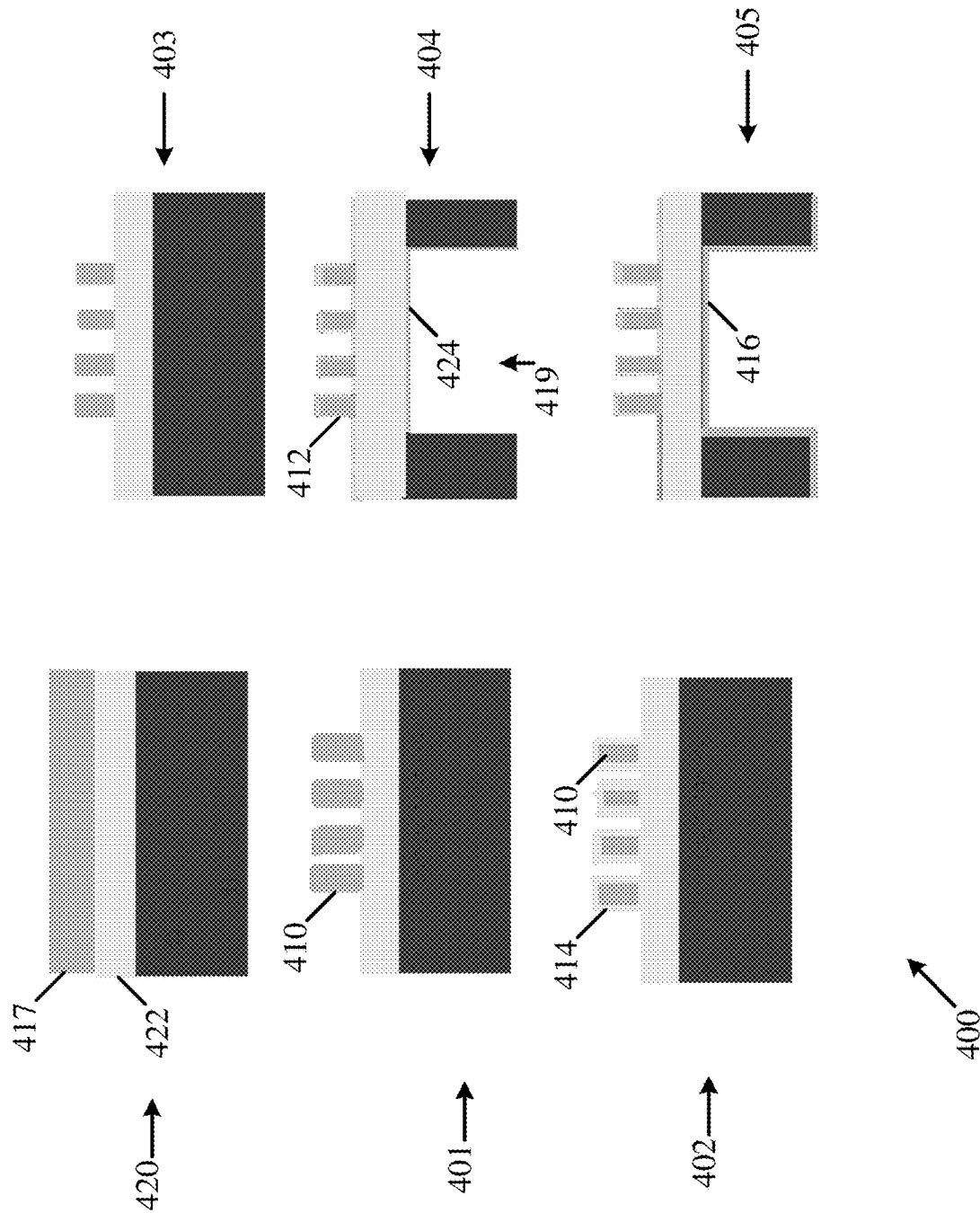
FIG. 4 is a schematic illustration of a fabrication process to fabricate an apparatus, in accordance with some demonstrative embodiments.

Reference is made to FIG. 4, which schematically illustrates a fabrication process 400 to fabricate an apparatus, in accordance with some demonstrative embodiments.

In one example, apparatus 200 (FIG. 2) and/or apparatus 300 (FIG. 3) may be fabricated, for example, based on one or more operations and/or fabrication stages of fabrication process 400.

In some demonstrative embodiments, fabrication process 400 may be performed over a SOI wafer 420.

In some demonstrative embodiments, SOI wafer 420 may include a BOX layer 422 and a silicon layer 417, e.g., the device layer.

In one example, SOI wafer 420 may have a thickness of 0.15-0.05 micron (um), and/or may include an N-type SOI, which may be doped in a range between 1E14 and 1E17 cm-3, for example, 1E16 cm-3.

In another example, SOI wafer 420 may have any other thickness and/or any other doping range.

In some demonstrative embodiments, fabrication process 400 may include a fabrication stage 401, which may include forming a silicon nanowire 410 from silicon layer 417.

In some demonstrative embodiments, the fabrication stage 410 may include patterning silicon layer 417, for example, using a photoresist procedure or a hard mask procedure, to create silicon nanowire 410.

In one example, a width, e.g., critical dimension (CDs), of silicon nanowire 410 may be between 0.05-0.15 um, for example, 0.1 um.

In another example, silicon nanowire 410 may have any other width.

In some demonstrative embodiments, fabrication process 400 may include a fabrication stage 402, which may include oxidizing silicon nanowire 410 to grow an oxide layer 414, for example, to decrease a size of silicon nanowire 410.

In one example, a thickness of grown oxide layer 414 may be in a range of 100-500 angstroms (A), for example, a thickness of 250 A.

In other example, oxide layer 414 may have any other thickness.

In some demonstrative embodiments, fabrication process 400 may include a fabrication stage 403, which may include etching off oxide layer 414, for example, to decrease the size of silicon nanowire 410.

In one example, a width and a height of silicon nanowire 410, for example, after the etching of oxide layer 414, may be about 500 A.

In another example, silicon nanowire 410 may have any other width and/or height after the etching.

In some demonstrative embodiments, fabrication process 400 may include a fabrication stage 404, which may include deposing a charged dielectric layer 412, e.g., an ONO layer or an ON layer, on one or more side, for example, on three sides, of silicon nanowire 410.

In some demonstrative embodiments, deposing the charged dielectric layer 412 may include forming an ONO layer or an ON layer, for example, on three sides of silicon nanowire 410.

In one example, deposing the ON layer may include forming a silicon nitride having a width between 100-200 A on top of a thermal silicon oxide layer having a width of about 70 A. In other embodiments, the silicon nitride and/or the thermal silicon oxide layer may have any other width.

In one example, deposing the ONO layer may include deposing a first thermal silicon oxide layer, e.g., by oxidation of Nitride or deposition of the oxide, on top of a silicon nitride layer, which is on top of a second thermal silicon oxide layer. For example, deposing the ONO layer may be similar to formation of an NROM layer.

In some demonstrative embodiments, as shown in FIG. 4, fabrication stage 404 may include removing a silicon layer from a backside of SOI wafer 420, for example, to create an opening 419 in the backside of SOI wafer 420, for example, using a mask procedure.

In some demonstrative embodiments, the opening 419 in the backside of SOI wafer 420 may form a backside gate 424 coupled to the silicon nanowire 410.

In one example, the BOX layer 422 may be used as an etch stop, for example, to create opening 419.

In some demonstrative embodiments, fabrication process 400 may include a fabrication stage 405, which may include a metal layer 416 at the back gate, for example, by deposing, e.g., sputtering, electroplating, and/or any other deposition technique.

In one example, metal layer 416 may include any metal, for example, suitable for thermal sensors.

In another example, metal layer 416 may include Palladium and/or Platinum, which may be configured to react with a predefined type of gas, for example, for catalytic combustion gas sensors.

In some demonstrative embodiments, metal layer 416 may be deposited at the front side of SOI wafer 420, e.g., in addition to or instead of, the backside of SOI wafer 420.

In one example, nanowire 410 may be formed of various materials, including silicon. However, silicon nanowires may be relatively easy integrated into products, which may be made in standard semiconductor processes.

In some demonstrative embodiments, a top-down approach may often be used in the fabrication of a silicon nanowire. For example, the SOI wafer 420 may be the starting material. The Silicon nanowire 410 may be formed in the silicon layer 417 of the SOI wafer 420, for example, by masking and etching silicon layer 417, e.g., as described above with reference to fabrication stages 402 and/or 404.

In one example, one or more Ohmic contacts, p-n junctions, and/or Schottky barriers may be coupled to an end of the silicon nanowire 410.

In one example, the silicon nanowire 410 may span like a beam over an etched area in the BOX layer 422. For example, the silicon nanowire 410 may be defined by dry etch and one or more processing stages may be carried out, for example, to modify the nanowire and/or to complete fabrication of the apparatus.

In some demonstrative embodiments, the silicon nanowire 410 may be oxidized and etched, for example, to remove the grown silicon dioxide 414, e.g., in order to make a body of the nanowire thinner, e.g., as described above with reference to fabrication stages 402 and/or 403.

In one example, a silicon nitride hard mask on intermediate ends of the silicon beam may be used, for example, to thin a middle of the silicon nanowire 410.

Figure 5:
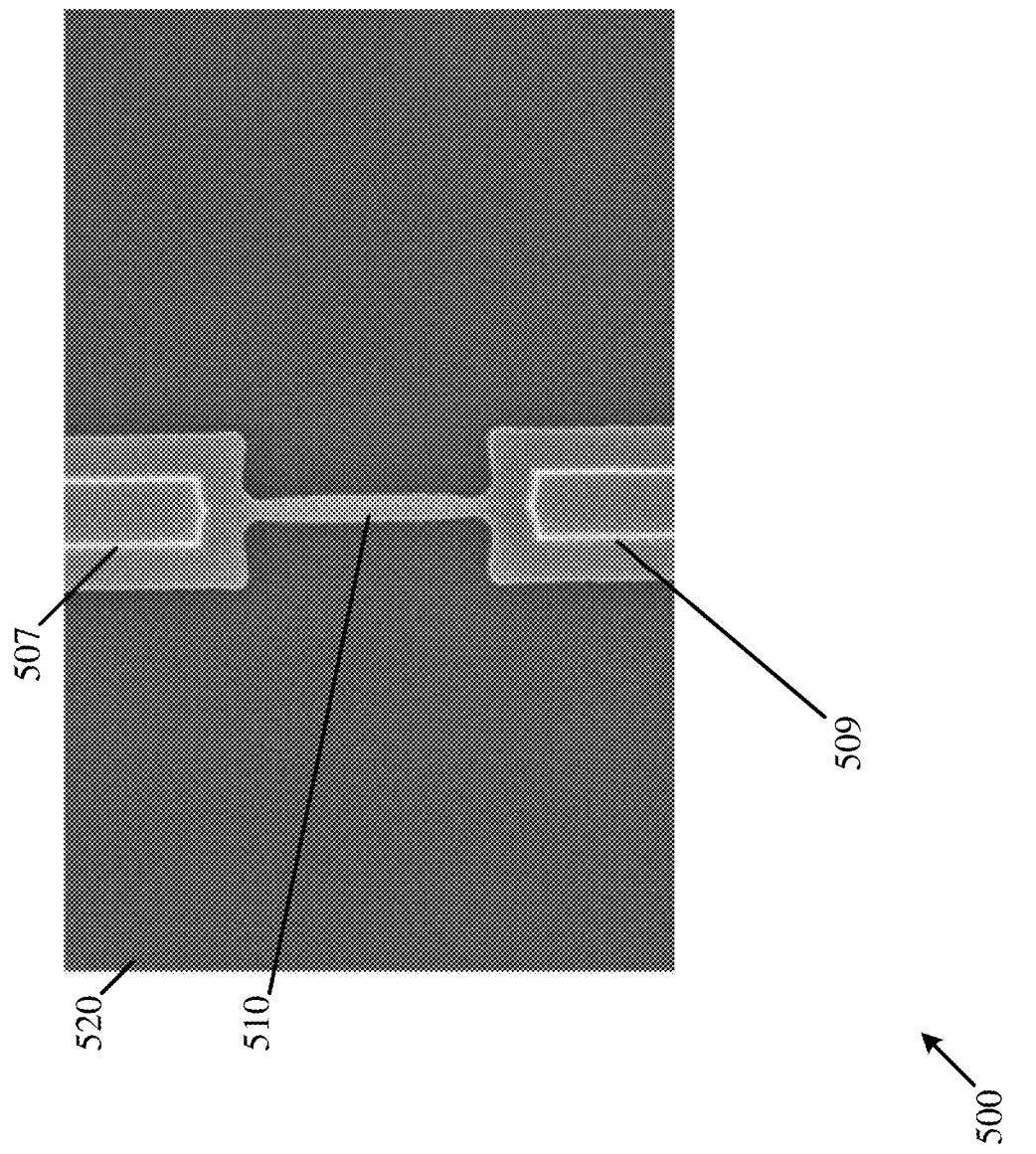
FIG. 5 is a top view image of an apparatus, in accordance with some demonstrative embodiments.

Reference is made to FIG. 5, which is a top view image of an apparatus 500, in accordance with some demonstrative embodiments.

In one example, the apparatus of FIG. 5 may include the apparatus 400 formed according to the fabrication process of FIG. 4.

In one example, apparatus 500 may include a temperature sensor and/or a gas sensor.

In some demonstrative embodiments, as shown in FIG. 5, apparatus 500 may include a silicon nanowire 510 on a SOI wafer 520.

In some demonstrative embodiments, as shown in FIG. 5, a first end of silicon nanowire 510 may be coupled to a first pad 507, and a second end of silicon nanowire 510 may be coupled to a second pad 509.

In some demonstrative embodiments, first pad 507 and second pad 509 may reside on SOI wafer 520.

In one example, silicon nanowire 510 may be operable as a heater, for example, when a heating current is to be driven between the first pad 507 and second pads 509 via the silicon nanowire 510.

In one example, as shown in FIG. 5, apparatus 500 may have a structure of a "dog bone" formed on a SOI having a diameter of between 500 A-1500 A. For example, apparatus 500 may be formed by wire definition, thinning and/or dielectric deposition.

In some demonstrative embodiments, an apparatus may include a silicon nanowire, which may not be on a silicon substrate, e.g., as described below.

In some demonstrative embodiments, the silicon nanowire may not be in contact with the silicon substrate, e.g., as described below.

In some demonstrative embodiments, a charged dielectric layer may cover four sides of the silicon nanowire, e.g., as described below.

In some demonstrative embodiments, the apparatus may include an open area in the silicon substrate, for example, under the silicon nanowire, e.g., as described below.

In some demonstrative embodiments, the apparatus may include, or may be operable as, a gas sensor, a temperature sensor, e.g., as described below.

Figure 6:
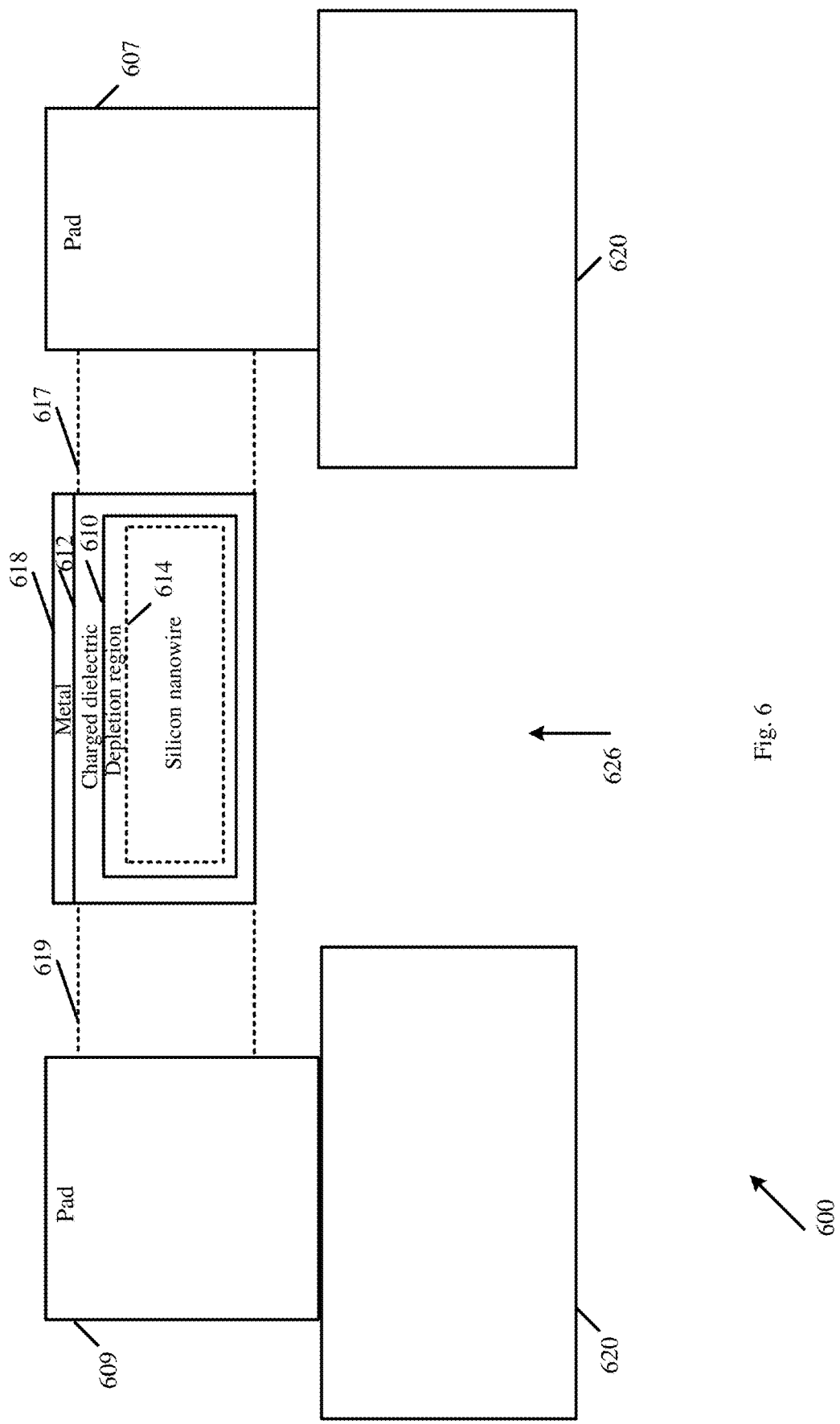
FIG. 6 is a schematic block diagram illustration of an apparatus, in accordance with some demonstrative embodiments.

Reference is made to FIG. 6, which schematically illustrates an apparatus 600, in accordance with some demonstrative embodiments.

In some demonstrative embodiments, apparatus 600 may include, or may be operable as, a gas sensor configured to sense a predefined type of gas, e.g., as described below.

In some demonstrative embodiments, as shown in FIG. 6, apparatus 600 may include a silicon nanowire 610, which may not be on a silicon substrate 620, e.g., as described below.

In some demonstrative embodiments, as shown in FIG. 6, the silicon nanowire 610 may not be in contact with the silicon substrate 620, e.g., as described below.

In some demonstrative embodiments, as shown in FIG. 6, apparatus 600 may include a first pad 607 on silicon substrate 620, e.g., as described below.

In some demonstrative embodiments, as shown in FIG. 6, apparatus 600 may include a second pad 609 on silicon substrate 620.

In some demonstrative embodiments, as shown in FIG. 6, silicon nanowire 610 may have a first end 617 coupled to the first pad 607.

In some demonstrative embodiments, as shown in FIG. 6, silicon nanowire 610 may have a second end 619 coupled to the second pad 609.

In some demonstrative embodiments, silicon nanowire 610 may be configured to drive a current between the first pad 607 and the second pad 609.

In some demonstrative embodiments, as shown in FIG. 6, apparatus 600 may include a charged dielectric layer 612 to cover the silicon nanowire 610.

In some demonstrative embodiments, charged dielectric layer 612 may cover four sides of the silicon nanowire 610.

In some demonstrative embodiments, as shown in FIG. 6, the charged dielectric layer 612 may be configured to create a depletion region 614 in a conductive channel of the silicon nanowire 610, e.g., as described below.

In some demonstrative embodiments, as shown in FIG. 6, apparatus 600 may include an open area 626 in the silicon substrate 620, for example, under the silicon nanowire 610.

In some demonstrative embodiments, as shown in FIG. 6, silicon nanowire 610 may be above open area 626, for example, while the first pad 607 and the second pad 609 may be on bulk silicon of silicon substrate 620.

In some demonstrative embodiments, as shown in FIG. 6, silicon nanowire 610 may be covered with a metal layer 618.

In one example, the metal layer 618 may cover an upper side of silicon nanowire 610.

In another example, the metal layer 618 may cover the upper side and/or the lower side of silicon nanowire 610.

In some demonstrative embodiments, the metal layer 618 may include, or may be at least partially formed of, at least Palladium and/or Platinum and/or any other type of material.

In some demonstrative embodiments, the metal layer 618 may be configured to react with a predefined type of gas.

In one example, the metal layer 618 may operate as a catalyst for gas sensing.

In some demonstrative embodiments, the metal layer 618 may operate as a backside sensing area and/or a backside sensing area, e.g., to sense gas at the backside and/or front side of silicon substrate 620.

In some demonstrative embodiments, as shown in FIG. 6, silicon nanowire 610 may be released, e.g., etched off, of a BOX layer of silicon substrate 620.

In some demonstrative embodiments, as shown in FIG. 6, charged dielectric layer 612, e.g., an ONO layer, may be deposited on one or more surfaces of silicon nanowire, e.g., all around silicon nanowire 610, and may be charged, e.g., by a UV light and/or by any other manner.

Figure 7:
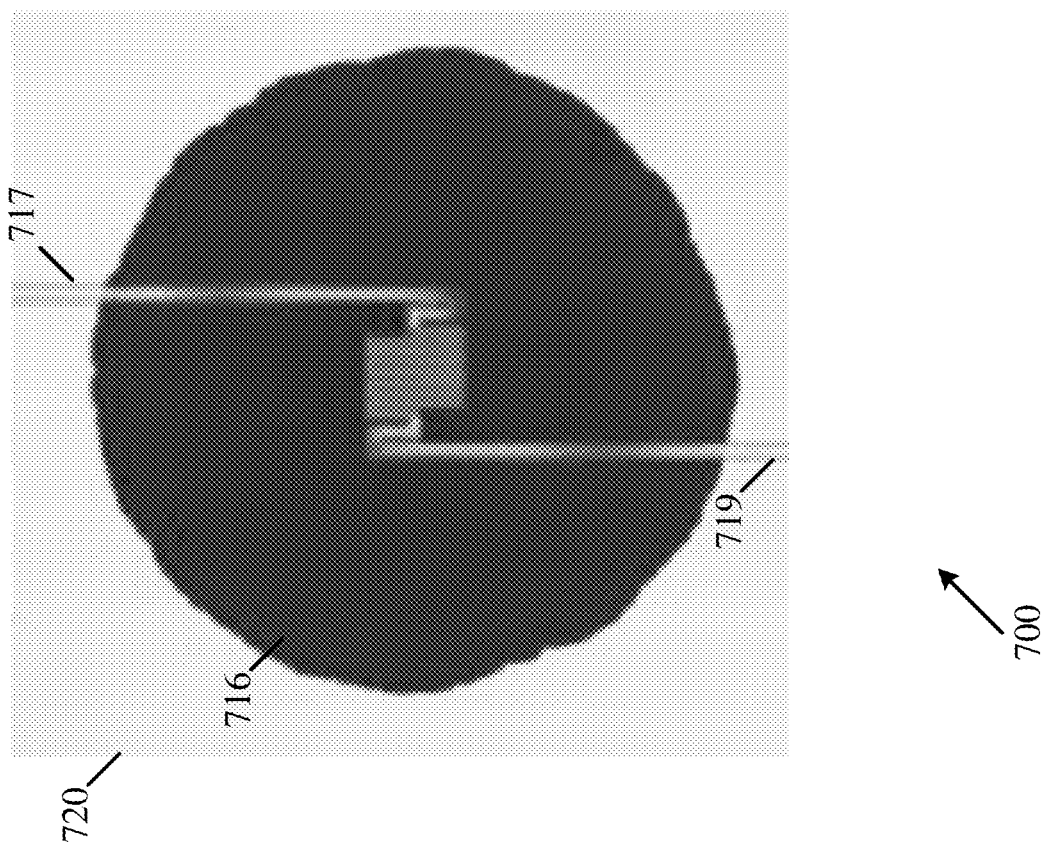
FIG. 7 is a top view image of an apparatus, in accordance with some demonstrative embodiments.

Reference is made to FIG. 7, which is a top view image of an apparatus 700, in accordance with some demonstrative embodiments.

In one example, apparatus 700 may include a temperature sensor or a gas sensor.

In one example, the apparatus of FIG. 7 may include apparatus 600 (FIG. 6).

In some demonstrative embodiments, as shown in FIG. 7, apparatus 700 may include a silicon nanowire 710 on top of a silicon substrate 720.

In one example, silicon nanowire 710 may be non-thinned.

In some demonstrative embodiments, as shown in FIG. 7, apparatus 700 may include an open area 716 in the silicon substrate 720, for example, under the silicon nanowire 710.

In one example, open area 716 may have a diameter of around 300 um. In another example, open area 716 may have any other diameter.

In some demonstrative embodiments, as shown in FIG. 7, silicon nanowire 710 may not be on silicon substrate 720.

In some demonstrative embodiments, as shown in FIG. 7, the silicon nanowire 720 may not be in contact with the silicon substrate 720.

In some demonstrative embodiments, as shown in FIG. 7, silicon nanowire 710 may have a first end 717, which may be coupled to a first pad, for example, pad 607 (FIG. 6), e.g., as described above.

In some demonstrative embodiments, as shown in FIG. 7, silicon nanowire 110 may have a second end 719, which may be coupled to a second pad, for example, pad 609 (FIG. 6), e.g., as described above.

In some demonstrative embodiments, the first pad and/or the second pad may reside on, e.g., may be in contact with, silicon substrate 720.

In some demonstrative embodiments, silicon nanowire 710 may be configured to drive a current between the first pad and the second pad, e.g., subject to the temperature, the presence of gas and/or any other trigger.

Referring back to FIG. 1, in some demonstrative embodiments, an apparatus including the silicon nanowire described herein, e.g., apparatus 100 and/or apparatus 600 (FIG. 6), may have an improved sensitivity, for example, by decreasing noises connected with Si—SiO2 interfaces.

In some demonstrative embodiments, the configuration of apparatus 100 (FIG. 1) and/or apparatus 600 (FIG. 6) may allow achieving a reduced noise level, e.g., an ultra-low noise level, for example, since the conductive channel of silicon nanowire 110 and/or 610 (FIG. 6) is separated from the silicon substrate, for example, by a charged dielectric layer 112 and/or 612, e.g., from all four sides.

In some demonstrative embodiments, the configuration of apparatus 100 (FIG. 1) and/or apparatus 600 (FIG. 6), as described above, may allow to simplify a design of temperature and/or gas sensors, and/or may reduce fabrication costs of corresponding devices.

In some demonstrative embodiments, the configuration of apparatus 100 (FIG. 1) and/or apparatus 600 (FIG. 6), as described above, may allow to provide a technical solution of trapping of charge in a charged dielectric layer, e.g., charged dielectric layer 112 (FIG. 1), surrounding a silicon nanowire, e.g., silicon nanowire 110 (FIG. 1), for controlling a position of the conductive channel, e.g., in silicon nanowire 110 (FIG. 1).

In some demonstrative embodiments, the configuration of apparatus 100 (FIG. 1) and/or apparatus 600 (FIG. 6), as described above, may allow to efficient sensing of a predefined type of gas. For example, the silicon nanowire may be covered with a catalyst functionalizing material, e.g., Palladium and/or Platinum, which may act as catalyst, for example, on one or both sides of silicon nanowire 110 (FIG. 1) and/or silicon nanowire 610 (FIG. 6).

In some demonstrative embodiments, the configuration of apparatus 100 (FIG. 1) may be implemented, for example, to enable a temperature sensor to be controlled by a metal back gate, e.g., backside gate 124 (FIG. 1), in combination with a charged dielectric layer, e.g., charged dielectric layer 112 (FIG. 1), and placed on a membrane.

In some demonstrative embodiments, the configuration of apparatus 100 (FIG. 1) may be implemented, for example, to provide a simple bias circuit, e.g., using backside gate 124.

In some demonstrative embodiments, the configuration of apparatus 100 (FIG. 1) may be implemented, for example, to provide increased temperature sensitivity.

Figure 8:
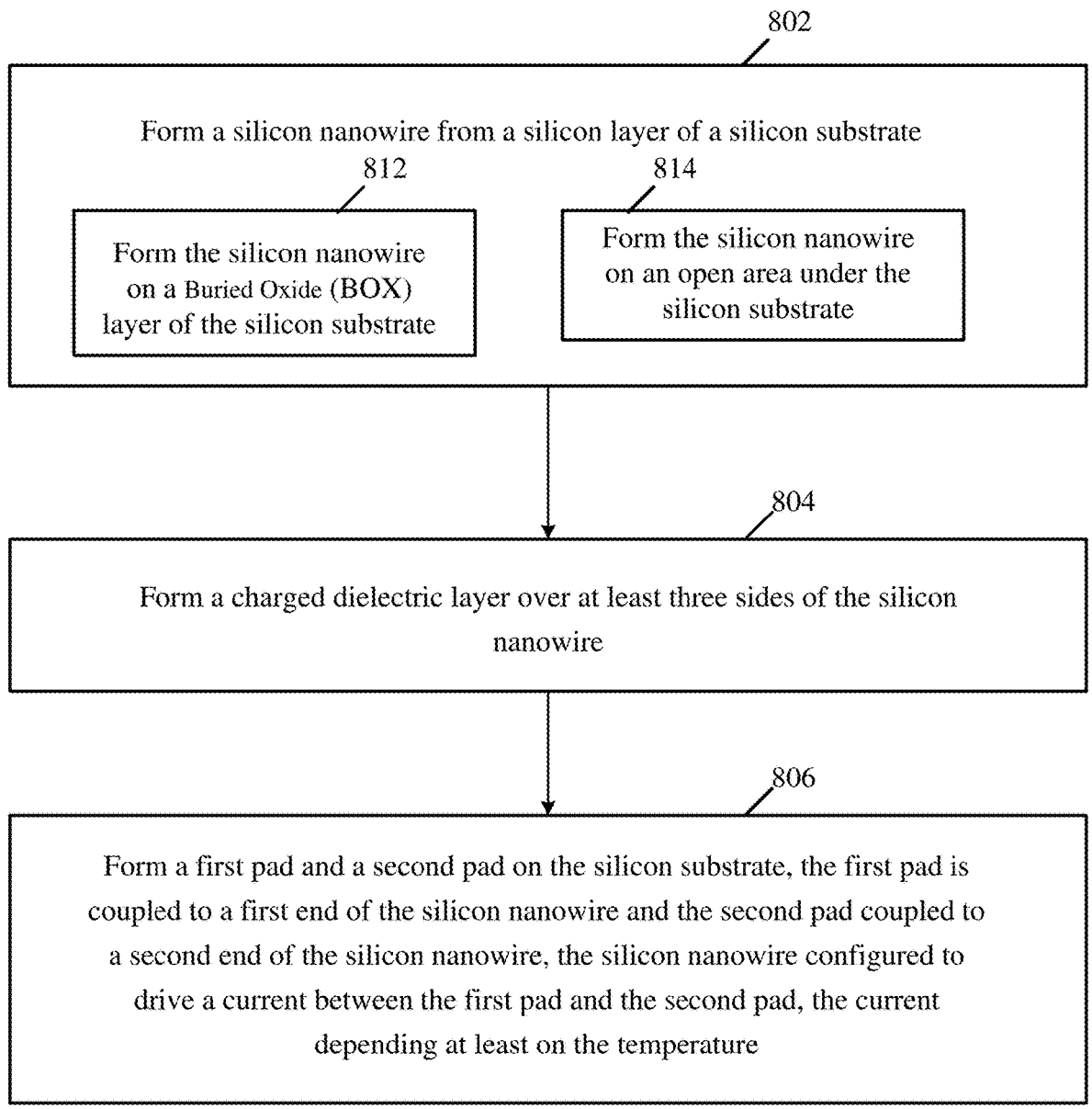
FIG. 8 is a schematic flow-chart illustration of a method of fabricating an apparatus, in accordance with some demonstrative embodiments.

Reference is made to FIG. 8, which schematically illustrates a method of fabricating an apparatus, in accordance with some demonstrative embodiments. For example, one or more of the operations of the method of FIG. 8 may be performed during a fabrication process of apparatus 100 (FIG. 1), apparatus 200 (FIG. 2), apparatus 300 (FIG. 3), apparatus 500 (FIG. 5), apparatus 600 (FIG. 6), and/or apparatus 700 (FIG. 1).

As indicated at block 802, the method may include forming a silicon nanowire from a silicon layer of a silicon substrate. For example, fabricating apparatus 100 (FIG. 1) may include forming silicon nanowire 110 (FIG. 1) from the silicon layer of silicon substrate 120 (FIG. 1); and/or fabricating apparatus 600 (FIG. 6) may include forming silicon nanowire 610 (FIG. 6) from the silicon layer of silicon substrate 620 (FIG. 6), e.g., as described above.

As indicated at block 804, the method may include forming a charged dielectric layer over at least three sides of the silicon nanowire. For example, fabricating apparatus 100 (FIG. 1) may include forming the charged dielectric layer 112 (FIG. 1) over three sides of the silicon nanowire 110 (FIG. 1); and/or fabricating apparatus 600 (FIG. 6) may include forming the charged dielectric layer 612 (FIG. 6) over four sides of the silicon nanowire 610 (FIG. 6), e.g., as described above.

As indicated at block 806, the method may include forming a first pad and a second pad on the silicon substrate, the first pad is coupled to a first end of the silicon nanowire and the second pad coupled to a second end of the silicon nanowire, the silicon nanowire configured to drive a current between the first pad and the second pad, the current depending at least on the temperature. For example, fabricating apparatus 100 (FIG. 1) may include forming first pad 107 (FIG. 1) and second pad 109 (FIG. 1) on the silicon substrate 120 (FIG. 1), the first pad 107 (FIG. 1) is coupled to the first end 117 (FIG. 1) of the silicon nanowire 110 (FIG. 1) and the second pad 109 (FIG. 1) is coupled to the second end 119 (FIG. 1) of the silicon nanowire 110 (FIG. 1) and the silicon nanowire 110 (FIG. 1) may be configured to drive the current, which is depending at least on the temperature, between the first pad 107 (FIG. 1) and the second pad 109 (FIG. 1), e.g., as described above. For example, fabricating apparatus 600 (FIG. 6) may include forming first pad 607 (FIG. 6) and second pad 609 (FIG. 6) on the silicon substrate 620 (FIG. 6), the first pad 609 (FIG. 6) is coupled to the first end 617 (FIG. 1) of the silicon nanowire 610 and the second pad 609 is coupled to the second end 619 (FIG. 1) of the silicon nanowire 610 (FIG. 6) and the silicon nanowire 610 (FIG. 6) may be configured to drive the current, which is depending at least on the temperature, between the first pad 607 (FIG. 6) and the second pad 609 (FIG. 6), e.g., as described above.

In some demonstrative embodiments, the method may include deposing a metal layer over one or more sides of the silicon nanowire. For example, fabricating apparatus 100 (FIG. 1) may include deposing the metal layer 118 (FIG. 1) over one or more sides of the silicon nanowire 110 (FIG. 1); and/or fabricating apparatus 600 (FIG. 6) may include deposing the metal layer 618 (FIG. 6) over one or more sides of the silicon nanowire 610 (FIG. 1), e.g., as described above.

In some demonstrative embodiments, forming the silicon nanowire may include forming the silicon nanowire using a photoresist procedure or a hard mask procedure. For example, fabricating apparatus 100 (FIG. 1) may include forming silicon nanowire 110 (FIG. 1) using the photoresist procedure or the hard mask procedure; and/or fabricating apparatus 600 (FIG. 6) may include forming silicon nanowire 610 (FIG. 6) using the photoresist procedure or the hard mask procedure, e.g., as described above.

In some demonstrative embodiments, forming the charged dielectric layer may include forming an ONO layer, or an ON layer, for example, if the silicon nanowire includes an N-type silicon nanowire. For example, forming the charged dielectric layer 112 (FIG. 1) may include forming the ONO layer, or the ON layer, for example, if the silicon nanowire 110 (FIG. 1) includes the N-type silicon nanowire, e.g., as described above.

In some demonstrative embodiments, forming the charged dielectric layer may include illuminating the ONO layer or the ON layer by UV light. For example, forming the charged dielectric layer 112 (FIG. 1) may include illuminating the ONO layer or the ON layer by the UV light, for example, if the silicon nanowire 110 (FIG. 1) includes the N-type silicon nanowire, e.g., as described above.

In some demonstrative embodiments, forming the charged dielectric layer may include forming a charged oxide layer, for example, if the silicon nanowire includes a P-type silicon nanowire. For example, forming the charged dielectric layer 112 (FIG. 1) may include forming the charged oxide layer, for example, if the silicon nanowire 110 (FIG. 1) includes the P-type silicon nanowire, e.g., as described below In some demonstrative embodiments, forming the charged dielectric layer may include irradiating the charged oxide layer by ionizing radiation. For example, forming the charged dielectric layer 112 (FIG. 1) may include irradiating the charged oxide layer by ionizing radiation, e.g., using gamma and/or X-rays, for example, if the silicon nanowire 110 (FIG. 1) includes the P-type silicon nanowire, e.g., as described above.

In some demonstrative embodiments, as indicated at block 812, forming the silicon nanowire may include forming the silicon nanowire on a BOX layer of a SOI substrate. For example, fabricating apparatus 100 (FIG. 1) may include forming silicon nanowire 110 (FIG. 1) on BOX layer 122 (FIG. 1), e.g., as described above.

In some demonstrative embodiments, the method may include forming a backside gate coupled to the silicon nanowire. For example, fabricating apparatus 100 (FIG. 1) may include forming backside gate 124 (FIG. 1) coupled to the silicon nanowire 110 (FIG. 1), e.g., as described above.

In some demonstrative embodiments, forming the silicon nanowire may include forming the silicon nanowire on a first side of the BOX layer of the SOI substrate, and forming the backside gate on a second side of the BOX layer, the second side opposite to the first side. For example, fabricating apparatus 100 (FIG. 1) may include forming the silicon nanowire 110 (FIG. 1) on the first side of BOX layer 122 (FIG. 1), and forming the backside gate 124 (FIG. 1) on the second side of the BOX layer 122 (FIG. 1), which is opposite to the first side, e.g., as described above.

In some demonstrative embodiments, forming the backside gate on the second side of the BOX may include forming an opening in the SOI substrate on the second side of the BOX layer. For example, forming the backside gate 124 (FIG. 1) may include forming opening 126 (FIG. 1) in the silicon substrate 120 (FIG. 1) on the second side of the BOX layer 122 (FIG. 1), e.g., as described above.

In some demonstrative embodiments, forming the backside gate may include deposing a metal layer. For example, forming the backside gate 124 (FIG. 1) may include deposing the metal layer 116 (FIG. 1), e.g., as described above.

In some demonstrative embodiments, forming the silicon nanowire may include oxidizing an initial silicon nanowire to grow oxide on the initial silicon nanowire, and etching the oxide. For example, fabrication process 400 (FIG. 4) may include oxidizing silicon nanowire 410 (FIG. 4) to grow oxide layer 414 (FIG. 4) on silicon nanowire 410 (FIG. 4), and etching oxide layer 414 (FIG. 4), e.g., as described above.

In some demonstrative embodiments, as indicated at block 814, forming the silicon nanowire may include forming an open area in the silicon substrate under the silicon nanowire. For example, fabricating apparatus 600 (FIG. 6) may include forming opening 626 (FIG. 6) under silicon nanowire 610 (FIG. 6), e.g., as described above.

In some demonstrative embodiments, forming the charged dielectric layer may include forming the charged dielectric layer over four sides of the silicon nanowire. For example, fabricating apparatus 600 (FIG. 6) may include forming the charged dielectric layer 612 (FIG. 6) over four sides of the silicon nanowire 610 (FIG. 6), e.g., as described above.

Figure 9:
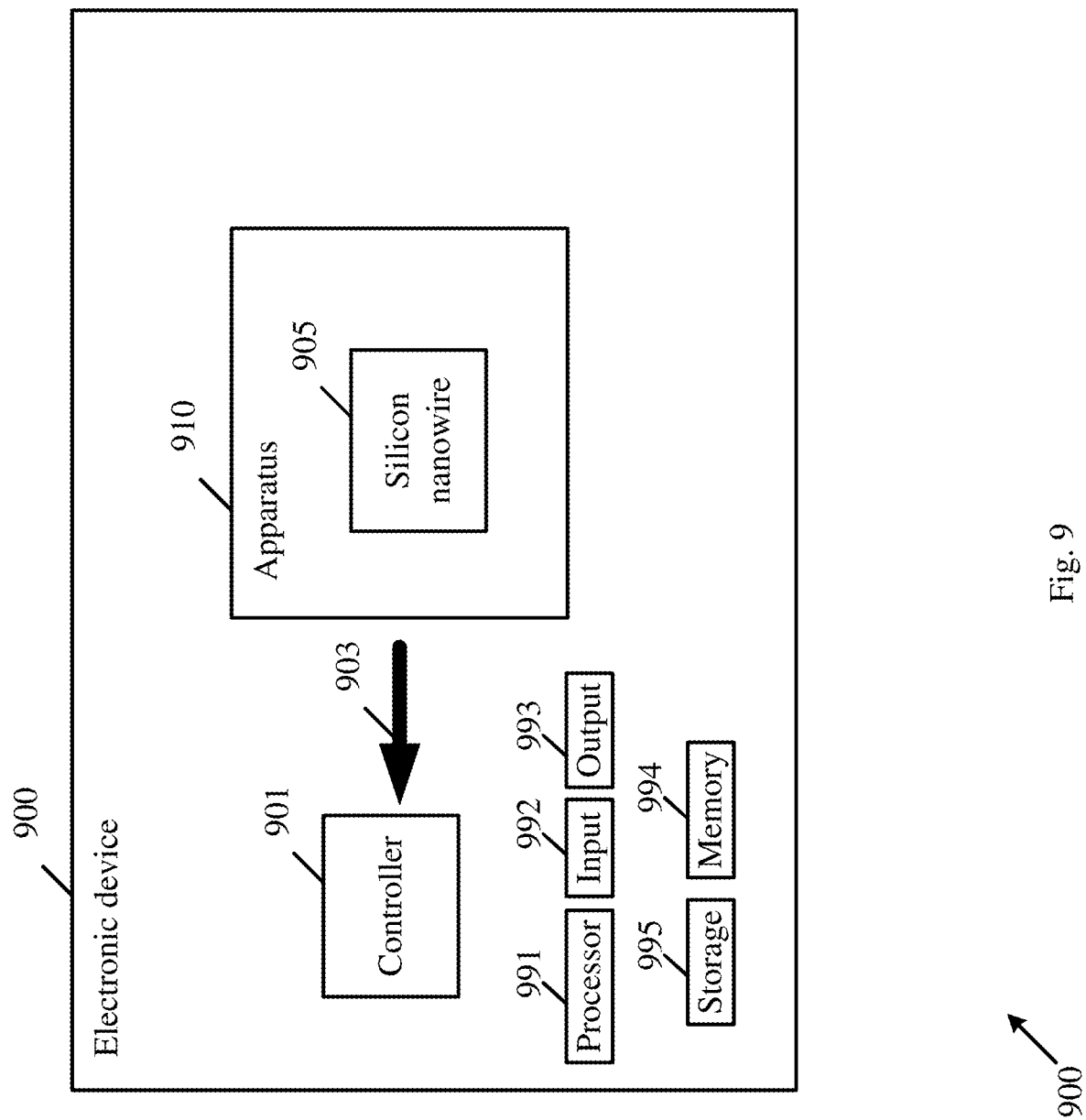
FIG. 9 is a schematic block diagram illustration of an electronic device, in accordance with some demonstrative embodiments.

Reference is made to FIG. 9, which schematically illustrates a block diagram of an electronic device 900, in accordance with some demonstrative embodiments.

In some demonstrative embodiments, electronic device 900 may include, for example, an IoT device.

In one example, electronic device 900 may include, for example, an IoT remote (mote), e.g., including a sensor and a transceiver to transmit one or more transmissions based on an output of the sensor.

In some demonstrative embodiments, electronic device 900 may include a temperature-sensing device.

In one example, electronic device 900 may include an IOT temperature-sensing device. For example, electronic device 900 may include an IOT temperature-sensing mote.

In some demonstrative embodiments, electronic device 900 may include a gas sensor.

In some demonstrative embodiments, the electronic device may include any other electronic device.

In some demonstrative embodiments, electronic device 900 may include or may be implemented as an Integrated Circuit (IC).

In some demonstrative embodiments, electronic device 900 may include an apparatus 910.

In some demonstrative embodiments, apparatus 900 may include one or more elements of, and/or may perform one or more operations, and/or one or more functionalities of, apparatus 100 (FIG. 1), apparatus 200 (FIG. 2), apparatus 300 (FIG. 3), apparatus 500 (FIG. 5), apparatus 600 (FIG. 6), and/or apparatus 700 (FIG. 1).

In some demonstrative embodiments, apparatus 910 may include, or may be operable as, a temperature sensor to sense the temperature.

In some demonstrative embodiments, apparatus 910 may include, or may be operable as, a gas sensor to sense gas of a predefined type.

In some demonstrative embodiments, apparatus 910 may include, or may be operable as, a heater configured to heat one or more elements, components, and/or units of electronic device 900.

In some demonstrative embodiments, electronic device 900 may include a controller 901 including circuitry configured to control electronic device 900 to perform one or more operations, for example, based on an output of apparatus 910.

In one example, controller 901 may control electronic device 900 to perform one or more operations, for example, based on a sensed temperature, which may be sensed by apparatus 910.

In another example, controller 901 may control electronic device 900 to perform one or more operations, for example, based on a detection of a predefined type of gas, which may be detected by apparatus 910.

In some demonstrative embodiments, apparatus 910 may include a silicon nanowire 910 configured to drive a current between a first pad and a second pad of apparatus 910, for example, the current may be depending at least on the temperature.

In some demonstrative embodiments, controller 901 may be configured to perform the one or more operations, for example, based on the current between the first pad and the second pad.

In some demonstrative embodiments, electronic device 900 may include a computing device, an electrical device, a mobile device, a mobile phone, a Smartphone, a tablet computer, a handheld computer, an Internet of Things (IoT) device, a power charging device, a sensor device, a sensing device, a handheld device, a wearable device, a gaming device, or the like.

In some demonstrative embodiments, electronic device 900 may also include, for example, one or more of a processor 991, an input unit 992, an output unit 993, a memory unit 994, and/or a storage unit 995. Electronic device 900 may optionally include other suitable hardware components and/or software components. In some demonstrative embodiments, some or all of the components of one or more of electronic device 900 may be enclosed in a common housing or packaging, and may be interconnected or operably associated using one or more wired or wireless links.

Examples

The following examples pertain to further embodiments.

Example 1 includes an apparatus of a temperature sensor to sense temperature, the apparatus comprising a first pad on a silicon substrate; a second pad on the silicon substrate; a silicon nanowire having a first end coupled to the first pad and a second end coupled to the second pad, the silicon nanowire configured to drive a current between the first pad and the second pad, the current depending at least on the temperature; and a charged dielectric layer covering at least three sides of the silicon nanowire.

Example 2 includes the subject matter of Example 1, and optionally, wherein the silicon nanowire is on the silicon substrate.

Example 3 includes the subject matter of Example 2, and optionally, wherein the silicon substrate comprises a silicon on insulator (SOI) substrate comprising a Buried Oxide (BOX) layer, the silicon nanowire is on the BOX layer.

Example 4 includes the subject matter of Example 3, and optionally, comprising a backside gate coupled to the silicon nanowire.

Example 5 includes the subject matter of Example 4, and optionally, wherein the backside gate is in contact with the BOX layer.

Example 6 includes the subject matter of Example 4 or 5, and optionally, wherein the backside gate is in an opening in the silicon substrate.

Example 7 includes the subject matter of any one of Examples 4-6, and optionally, wherein the backside gate is operable to control a size of a depletion region in a conductive channel of the silicon nanowire.

Example 8 includes the subject matter of any one of Examples 4-7, and optionally, wherein the backside gate comprises a metal layer.

Example 9 includes the subject matter of Example 8, and optionally, wherein the metal layer comprises at least one of Palladium or Platinum.

Example 10 includes the subject matter of Example 8 or 9, and optionally, wherein the metal layer is configured to react with a predefined type of gas.

Example 11 includes the subject matter of Example 1, and optionally, wherein the silicon nanowire is not in contact with the silicon substrate.

Example 12 includes the subject matter of Example 11, and optionally, wherein the charged dielectric layer covers four sides of the silicon nanowire.

Example 13 includes the subject matter of Example 11 or 12, and optionally, comprising an open area in the silicon substrate under the silicon nanowire.

Example 14 includes the subject matter of any one of Examples 1-13, and optionally, wherein the charged dielectric layer is configured to create a depletion region in a conductive channel of the silicon nanowire.

Example 15 includes the subject matter of any one of Examples 1-14, and optionally, wherein the silicon nanowire is covered with a metal layer.

Example 16 includes the subject matter of Example 15, and optionally, wherein the metal layer comprises at least one of Palladium or Platinum.

Example 17 includes the subject matter of Example 15 or 16, and optionally, wherein the metal layer is configured to react with a predefined type of gas.

Example 18 includes the subject matter of any one of Examples 1-17, and optionally, wherein the silicon nanowire is configured to be operable as a heater when a heating current is to be driven between the first and second pads via the silicon nanowire.

Example 19 includes the subject matter of any one of Examples 1-18, and optionally, wherein the silicon nanowire comprises an N-type silicon nanowire.

Example 20 includes the subject matter of Example 19, and optionally, wherein the charged dielectric layer comprises an Oxide Nitride Oxide (ONO) layer, or an Oxide Nitride (ON) layer.

Example 21 includes the subject matter of Example 20, and optionally, wherein the charged dielectric layer comprises an Ultra Violet (UV)-charged ONO layer, or a UV-charged ON layer.

Example 22 includes the subject matter of any one of Examples 1-18, and optionally, wherein the silicon nanowire comprises a P-type silicon nanowire.

Example 23 includes the subject matter of Example 22, and optionally, wherein the charged dielectric layer comprises a charged silicon dioxide layer.

Example 24 includes the subject matter of Example 23, and optionally, wherein the charged dielectric layer comprises an ionizing radiation charged silicon dioxide layer.

Example 25 includes the subject matter of any one of Examples 1-24, and optionally, wherein the silicon substrate comprises a silicon on insulator (SOI) substrate.

Example 26 includes a method of fabricating an apparatus of a temperature sensor to sense temperature, the method comprising forming a silicon nanowire from a silicon layer of a silicon substrate; forming a charged dielectric layer over at least three sides of the silicon nanowire; and forming a first pad and a second pad on the silicon substrate, the first pad is coupled to a first end of the silicon nanowire and the second pad coupled to a second end of the silicon nanowire, the silicon nanowire configured to drive a current between the first pad and the second pad, the current depending at least on the temperature.

Example 27 includes the subject matter of Example 26, and optionally, comprising forming a backside gate coupled to the silicon nanowire.

Example 28 includes the subject matter of Example 27, and optionally, comprising forming the silicon nanowire on a first side of a Buried Oxide (BOX) layer of a Silicon On Insulator (SOI) substrate, and forming the backside gate on a second side of the BOX layer, the second side opposite to the first side.

Example 29 includes the subject matter of Example 27 or 28, and optionally, wherein forming the backside gate on the second side of the BOX comprises forming an opening in the SOI substrate on the second side of the BOX layer.

Example 30 includes the subject matter of any one of Examples 27-29, and optionally, wherein the backside gate is operable to control a size of a depletion region in a conductive channel of the silicon nanowire.

Example 31 includes the subject matter of any one of Examples 27-30, and optionally, wherein forming the backside gate comprises deposing a metal layer.

Example 32 includes the subject matter of any one of Examples 26-31, and optionally, comprising deposing a metal layer over one or more sides of the silicon nanowire.

Example 33 includes the subject matter of any one of Examples 31 or 32, and optionally, wherein the metal layer comprises at least one of Palladium or Platinum.

Example 34 includes the subject matter of any one of Examples 31-33, and optionally, wherein the metal layer is configured to react with a predefined type of gas.

Example 35 includes the subject matter of Example 26, and optionally, wherein forming the silicon nanowire comprises forming an open area in the silicon substrate under the silicon nanowire.

Example 36 includes the subject matter of Example 35, and optionally, comprising forming the charged dielectric layer over four sides of the silicon nanowire.

Example 37 includes the subject matter of any one of Examples 26-36, and optionally, wherein the charged dielectric layer is configured to create a depletion region in a conductive channel of the silicon nanowire.

Example 38 includes the subject matter of any one of Examples 26-37, and optionally, wherein the silicon nanowire comprises an N-type silicon nanowire, forming the charged dielectric layer comprises forming an Oxide Nitride Oxide (ONO) layer, or an Oxide Nitride (ON) layer.

Example 39 includes the subject matter of Example 38, and optionally, wherein forming the charged dielectric layer comprises illuminating the ONO layer or the ON layer by Ultra Violet (UV) light.

Example 40 includes the subject matter of any one of Examples 26-37, and optionally, wherein the silicon nanowire comprises a P-type silicon nanowire, forming the charged dielectric layer comprises forming a charged oxide layer.

Example 41 includes the subject matter of Example 40, and optionally, wherein forming the charged dielectric layer comprises irradiating the charged oxide layer by ionizing radiation.

Example 42 includes the subject matter of any one of Examples 26-41, and optionally, wherein forming the silicon nanowire comprises oxidizing an initial silicon nanowire to grow oxide on the initial silicon nanowire, and etching the oxide.

Example 43 includes the subject matter of Example any one of Examples 26-42, and optionally, wherein forming the silicon nanowire comprises forming the silicon nanowire using a photoresist procedure or a hard mask procedure.

Example 44 includes the subject matter of any one of Examples 26-43, and optionally, wherein the silicon substrate comprises a Silicon On Insulator (SOI) substrate.

Example 45 includes an electronic device comprising a temperature sensor to sense temperature, the temperature sensor comprising a first pad on a silicon substrate; a second pad on the silicon substrate; a silicon nanowire having a first end coupled to the first pad; and a second end coupled to the second pad, the silicon nanowire configured to drive a current between the first pad and the second pad, the current depending at least on the temperature; and a charged dielectric layer covering at least three sides of the silicon nanowire; and a controller comprising circuitry to perform one or more operations based on the current.

Example 46 includes the subject matter of Example 45, and optionally, wherein the silicon nanowire is on the silicon substrate.

Example 47 includes the subject matter of Example 46, and optionally, wherein the silicon substrate comprises a silicon on insulator (SOI) substrate comprising a Buried Oxide (BOX) layer, the silicon nanowire is on the BOX layer.

Example 48 includes the subject matter of Example 47, and optionally, wherein the temperature sensor comprises a backside gate coupled to the silicon nanowire.

Example 49 includes the subject matter of Example 48, and optionally, wherein the backside gate is in contact with the BOX layer.

Example 50 includes the subject matter of Example 48 or 49, and optionally, wherein the backside gate is in an opening in the silicon substrate.

Example 51 includes the subject matter of any one of Examples 48-50, and optionally, wherein the backside gate is operable to control a size of a depletion region in a conductive channel of the silicon nanowire.

Example 52 includes the subject matter of any one of Examples 48-51, and optionally, wherein the backside gate comprises a metal layer.

Example 53 includes the subject matter of Example 52, and optionally, wherein the metal layer comprises at least one of Palladium or Platinum.

Example 54 includes the subject matter of Example 52 or 53, and optionally, wherein the metal layer is configured to react with a predefined type of gas.

Example 55 includes the subject matter of Example 45, and optionally, wherein the silicon nanowire is not in contact with the silicon substrate.

Example 56 includes the subject matter of Example 55, and optionally, wherein the charged dielectric layer covers four sides of the silicon nanowire.

Example 57 includes the subject matter of Example 55 or 56, and optionally, wherein the temperature sensor comprises an open area in the silicon substrate under the silicon nanowire.

Example 58 includes the subject matter of any one of Examples 45-57, and optionally, wherein the charged dielectric layer is configured to create a depletion region in a conductive channel of the silicon nanowire.

Example 59 includes the subject matter of any one of Examples 45-58, and optionally, wherein the silicon nanowire is covered with a metal layer.

Example 60 includes the subject matter of Example 59, and optionally, wherein the metal layer comprises at least one of Palladium or Platinum.

Example 61 includes the subject matter of Example 59 or 60, and optionally, wherein the metal layer is configured to react with a predefined type of gas.

Example 62 includes the subject matter of any one of Examples 45-61, and optionally, wherein the silicon nanowire is configured to be operable as a heater when a heating current is to be driven between the first and second pads via the silicon nanowire.

Example 63 includes the subject matter of any one of Examples 45-62, and optionally, wherein the silicon nanowire comprises an N-type silicon nanowire.

Example 64 includes the subject matter of Example 63, and optionally, wherein the charged dielectric layer comprises an Oxide Nitride Oxide (ONO) layer, or an Oxide Nitride (ON) layer.

Example 65 includes the subject matter of Example 64, and optionally, wherein the charged dielectric layer comprises an Ultra Violet (UV)-charged ONO layer, or a UV-charged ON layer.

Example 66 includes the subject matter of any one of Examples 45-62, and optionally, wherein the silicon nanowire comprises a P-type silicon nanowire.

Example 67 includes the subject matter of Example 66, and optionally, wherein the charged dielectric layer comprises a charged silicon dioxide layer.

Example 68 includes the subject matter of Example 67, and optionally, wherein the charged dielectric layer comprises an ionizing radiation charged silicon dioxide layer.

Example 69 includes the subject matter of any one of Examples 45-68, and optionally, wherein the silicon substrate comprises a silicon on insulator (SOI) substrate.

Example 70 includes the subject matter of any one of Examples 45-69, and optionally, comprising an Internet Of Things (IOT) device.

Example 71 includes the subject matter of any one of Examples 45-70, and optionally, comprising a gas sensor.

Functions, operations, components and/or features described herein with reference to one or more embodiments, may be combined with, or may be utilized in combination with, one or more other functions, operations, components and/or features described herein with reference to one or more other embodiments, or vice versa.

While certain features have been illustrated and described herein, many modifications, substitutions, changes, and equivalents may occur to those skilled in the art. It is, therefore, to be understood that the appended claims are intended to cover all such modifications and changes as fall within the true spirit of the disclosure.

What is claimed is:

1. An apparatus of a temperature sensor to sense temperature, the apparatus comprising:
    a first pad on a silicon substrate;
    a second pad on the silicon substrate;
    a silicon nanowire having a first end coupled to the first pad and a second end coupled to the second pad, the silicon nanowire configured to drive a current between the first pad and the second pad, the current depending at least on the temperature; and
    a charged dielectric layer covering at least three sides of the silicon nanowire, wherein the charged dielectric layer comprises a dielectric layer comprising an electric charge to create a depletion region in the silicon nanowire.

2. The apparatus of claim 1, wherein the silicon nanowire is on the silicon substrate.

3. The apparatus of claim 2, wherein the silicon substrate comprises a silicon on insulator (SOI) substrate comprising a Buried Oxide (BOX) layer, the silicon nanowire is on the BOX layer.

4. The apparatus of claim 3 comprising a backside gate coupled to the silicon nanowire.

5. The apparatus of claim 4, wherein the backside gate is in contact with said BOX layer.

6. The apparatus of claim 4, wherein the backside gate is in an opening in the silicon substrate.

7. The apparatus of claim 4, wherein the backside gate is operable to control a size of the depletion region in a conductive channel of said silicon nanowire.

8. The apparatus of claim 4, wherein the backside gate comprises a metal layer.

9. The apparatus of claim 1, wherein the silicon nanowire is not in contact with the silicon substrate.

10. The apparatus of claim 9, wherein the charged dielectric layer covers four sides of the silicon nanowire.

11. The apparatus of claim 9 comprising an open area in the silicon substrate under the silicon nanowire.

12. The apparatus of claim 1, wherein the charged dielectric layer is configured to create the depletion region in a conductive channel of said silicon nanowire.

13. The apparatus of claim 1, wherein the silicon nanowire is covered with a metal layer.

14. The apparatus of claim 13, wherein the metal layer is configured to react with a predefined type of gas.

15. The apparatus of claim 1, wherein the silicon nanowire is configured to be operable as a heater when a heating current is to be driven between said first and second pads via said silicon nanowire.

16. The apparatus of claim 1, wherein the silicon nanowire comprises an N-type silicon nanowire, and the charged dielectric layer comprises a negative charge.

17. The apparatus of claim 16, wherein the charged dielectric layer comprises an Oxide Nitride Oxide (ONO) layer, or an Oxide Nitride (ON) layer.

18. The apparatus of claim 1, wherein the silicon nanowire comprises a P-type silicon nanowire, and the charged dielectric layer comprises a positive charge.

19. The apparatus of claim 18, wherein the charged dielectric layer comprises a charged silicon dioxide layer.

20. An electronic device comprising:
a temperature sensor to sense temperature, the temperature sensor comprising:
  a first pad on a silicon substrate;
  a second pad on the silicon substrate;
  a silicon nanowire having a first end coupled to the first pad; and a second end coupled to the second pad, the silicon nanowire configured to drive a current between the first pad and the second pad, the current depending at least on the temperature; and
  a charged dielectric layer covering at least three sides of the silicon nanowire, wherein the charged dielectric layer comprises a dielectric layer comprising an electric charge to create a depletion region in the silicon nanowire; and
a controller comprising circuitry to perform one or more operations based on said current.

21. The electronic device of claim 20 comprising a gas sensor.

* * * * *